(12) United States Patent
Willson-Hackworth et al.

(10) Patent No.: US 6,647,802 B2
(45) Date of Patent: Nov. 18, 2003

(54) CREEP TESTING FIXTURE AND METHOD

(75) Inventors: Kelly Willson-Hackworth, Pearland, TX (US); Steven George Luckey, Jr., Ann Arbor, MI (US); Daniel Q. Houston, Dearborn, MI (US); Edward M. Hagerman, Royal Oak, MI (US); John M. Henshaw, Tulsa, OK (US)

(73) Assignee: Automotive Composites Consortium, Tulsa, OK (US)

( * ) Notice: Subject to any disclaimer, the term of this patent is extended or adjusted under 35 U.S.C. 154(b) by 0 days.

(21) Appl. No.: 09/821,280

(22) Filed: Mar. 29, 2001

(65) Prior Publication Data

US 2002/0095995 A1 Jul. 25, 2002

Related U.S. Application Data

(60) Provisional application No. 60/193,799, filed on Mar. 31, 2000.

(51) Int. Cl.[7] ................................................ G01N 3/08
(52) U.S. Cl. ............................ 73/826; 73/789; 73/796; 73/856; 73/788
(58) Field of Search .......................... 73/826, 781, 862, 73/856, 789, 796, 806, 825, 837, 818, 788

(56) References Cited

U.S. PATENT DOCUMENTS

| | | | | |
|---|---|---|---|---|
| 3,884,504 A | * | 5/1975 | Campbell | 280/446 |
| 3,966,181 A | * | 6/1976 | Lessard | 267/58 |
| 4,430,884 A | * | 2/1984 | Landrigan | 73/4 |
| 5,798,463 A | | 8/1998 | Doudican et al. | |

* cited by examiner

*Primary Examiner*—Andrew H. Hirshfeld
*Assistant Examiner*—Marissa Ferguson
(74) *Attorney, Agent, or Firm*—Reising, Ethington, Barnes, Kisselle, P.C.

(57) ABSTRACT

A creep testing fixture and method for applying a precise amount of constant tensile stress to a creep test specimen to allow for precise measurement of creep in the test specimen. The fixture includes first and second mounting grips for holding opposite ends of a test specimen. A frame supports the mounting grips for relative reciprocal movement toward and away from each other. A tensile spring is connected between the first and second mounting grips. The frame subjects a test specimen held between the mounting grips to tensile stress in response to axially inward force that the tensile spring applies to the frame.

16 Claims, 3 Drawing Sheets

CREEP TESTING FIXTURE AND METHOD

This application claims the benefit of Provisional Application No. 60/193,799, filed Mar. 31, 2000.

TECHNICAL FIELD

This invention relates generally to creep testing fixtures and methods and, more particularly, to test fixtures and methods for measuring creep and creep recovery in tensile test specimens under a variety of environmental conditions.

BACKGROUND OF THE INVENTION

The characterization of creep, or time-dependent strain, is an important part of the development of polymers and polymer-matrix composite materials. The measurement of creep recovery, or strain decrease after load removal, is also an important part of composite material development. This is because polymers and polymer composites used on ground vehicles must have adequate creep resistance to maintain their dimensional integrity throughout their anticipated road life.

The rate at which a material creeps is a function of stress, temperature and environment. In addition, polymers and polymer composites are often subject to significant specimen-to-specimen variation in creep resistance, thus necessitating the testing of multiple specimens under identical environmental conditions to assure the statistical significance of results.

Currently, creep testing is done on stationary dead-weight creep machines. These dead weight creep machines are large and expensive. In addition, it is seldom practical to use such devices in the field.

A previous test fixture disclosed in U.S. Pat. No. 5,798,463, which issued Aug. 25, 1998, discloses a constant stress/constant strain testing fixture including first and second mounting grips for holding opposite ends of a test specimen. A frame supports the first and second mounting grips for relative reciprocal movement toward and away from each other. The frame comprises a pivoted lever arm frame structure that includes a compression column connected between first and second generally parallel lever arms. The first and second mounting grips are supported on the first and second lever arms, respectively. A compression spring is connected between the first and second mounting grips. More specifically, the compression spring is connected at one end to the first lever arm and at a second end to the second lever arm. The mounting grips are supported between the lever arms at respective points along the lever arms so that a test specimen held between the grips is positioned between and generally parallel to the compression column and the compression spring. This configuration subjects a test specimen held between the mounting grips to tensile stress in response to the axial outward force that the compression spring applies to the mounting grips.

The above constant stress/constant strain fixture was designed to apply stress to a test specimen as the specimen was being exposed to elevated temperatures and/or environmental fluids. Such testing was necessary in view of well-documented observations that environmental agents attack certain materials, such as polymer-based composites, more aggressively when those materials are under stress than when the materials are in an unloaded state. Since all structural applications of these materials include exposure to varying elevated stress levels it was imperative that the behavior of these materials be evaluated using such constant stress/constant strain devices. The device disclosed in U.S. Pat. No. 5,798,463 includes parallel lever arms and a relatively stiff, high-rate compression spring (defined as exerting a relatively large amount of force per unit of deflection) located between the lever arms to subject the test specimen to stress. In tests using these fixtures a test specimen was exposed for a prescribed time to environmental agents while under stress and was then tested to determine to what extent its residual physical/mechanical properties had decayed. While the constant stress/constant strain fixture is completely adequate for its designed purpose, it suffers from a significant shortcoming: that a specimen tested in the constant stress/constant strain fixture will respond to exposure to environmental agents by undergoing stress relaxation due to axial stretching. This, in turn, allows the compression spring to expand and consequently reduces the amount of stress the compression spring applies to the test specimen.

What is needed is a conceptually new creep-testing fixture designed around both the characteristics of spring loaded stressing fixtures and the creep characteristics of structural materials. Based on experience with structural applications of polymers and polymer-based composites, a creep strain boundary condition of 0.5% creep in a 3000 hour creep test has been established. A test specimen material under any combination of stress and environmental agents that exhibits greater than 0.5% creep strain in a 3000 hour creep test is unacceptable and would not be useable in applications under those conditions. With this boundary condition as the basis for selecting material to be used in anticipated applications, the design of a creep fixture to test such material would need to apply an acceptable level of stress to a test sample of the material while accepting a maximum of 0.5% of the applied creep stress. The test fixture must also be sufficiently compact in geometry to permit under-vehicle road testing.

SUMMARY OF THE INVENTION

The invention is a creep-testing fixture for applying a precise amount of constant tensile stress to a creep test specimen to allow for precise measurement of creep in the test specimen. The fixture includes first and second mounting grips for holding opposite ends of a test specimen and a frame supporting the first and second mounting grips for relative reciprocal movement toward and away from each other. A spring is connected between the first and second mounting grips. The frame is configured to subject a test specimen held between the mounting grips to tensile stress in response to force that the spring applies to the frame.

Unlike the prior art of record, the spring of the creep testing fixture is a tensile spring and the frame is configured to subject a test specimen to tensile stress in response to axially inward force that the tensile spring applies to the frame. This limits spring load loss over time by an amount sufficient to allow for accurate tensile creep testing of a test specimen. Tensile springs can be stretched extensively to produce a desired amount of creep stress that is limited only by the spring material yield strength. An equivalent compression spring would be unsuited for use in compact creep testing fixtures because it could only be compressed only a relatively short distance before its coils would come into contact with each other and relieve stress on the test specimen.

The invention also includes a method for applying a precise amount of constant tensile stress to a creep test specimen to allow for precise measurement of creep in the test specimen. According to this method one can applying a precise amount of constant tensile stress to a creep test specimen to allow for precise measurement of creep in the test specimen by connecting opposite ends of the tensile test specimen to the respective first and second mounting grips. Opposite ends of the spring are then connected to respective spring attachment points on the lever arms such that the spring applies a generally constant axial inward load to the lever arms and the lever arms apply a generally constant tensile load to the test specimen.

The invention also includes a method of measuring creep recovery that includes connecting opposite ends of the tensile test specimen to the respective first and second mounting grips then connecting opposite ends of the spring to respective spring attachments points on the lever arms such that the spring applies a generally constant axial inward load to the lever arms and the lever arms apply a generally constant tensile load to the test specimen. The resulting strain exhibited in the test specimen is then measured, the spring is returned to a relaxed condition and any resulting decrease in strain exhibited in the test specimen is measured.

BRIEF DESCRIPTION OF THE DRAWINGS

Other advantages of the present invention will be readily appreciated, as the same become better understood by reference to the detailed description when considered in connection with the accompanying drawings wherein.

DETAILED DESCRIPTION

Figure 1:
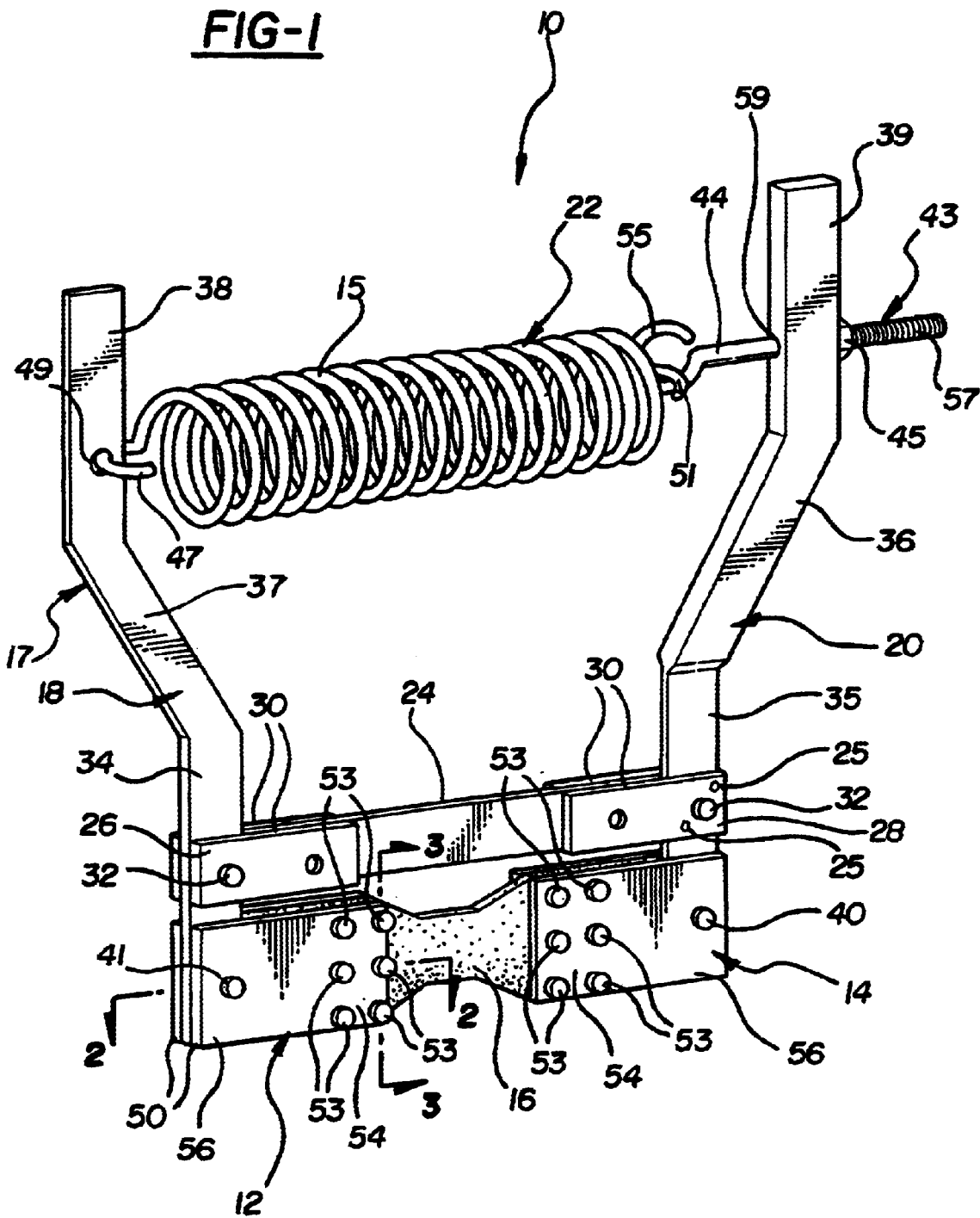
FIG. 1 is a perspective view of a tensile fixture constructed according to the present invention.

A composite creep testing fixture for applying a precise amount of constant tensile stress to a creep test specimen 16 to allow for precise measurement of creep in the test specimen 16 is shown at 10 in the drawings. The fixture 10 includes first and second mounting grips 12, 14 for holding opposite ends of a test specimen 16 and a frame 17 supporting the first and second mounting grips 12, 14 for relative reciprocal movement toward and away from each other. The fixture 10 also includes a spring 15 connected between the first and second mounting grips 12, 14, the frame 17 being configured to subject a test specimen 16 held between the mounting grips 12, 14 to tensile stress in response to force that the spring 15 applies to the frame 17. The spring 15 is a tensile spring and the frame 17 is configured to subject a test specimen 16 to tensile stress in response to axially inward force that the tensile spring 15 applies to the frame 17. The use of a tensile spring limits spring load loss over time by an amount sufficient to allow for accurate tensile creep testing of the test specimen 16.

The frame 17 comprises a pivoted lever arm frame structure that includes first and second lever arms 18, 20 and a compression column 24. The compression column 24 is connected between the first and second lever arms 18, 20. The spring 15 is also connected between the first and second lever arms 18, 20. The first and second mounting grips 12, 14 are supported on the first and second lever arms 18, 20 at respective points along the lever arms 18, 20 so that the compression column 24 is positioned between and generally parallel to the spring 15 and a test specimen 16 held between the grips 12, 14. This configuration subjects a test specimen 16 held between the mounting grips 12, 14 to tensile stress in response to the axial inward force that the tensile spring L5 applies to the lever arms 18, 20.

The compression column 24 is pivotally connected at a first end 26 to the first lever arm 18. As best shown in FIG. 1, a second end 28 of the compression column 24 is rigidly connected to the second lever arm 20 in a generally perpendicular orientation relative to the second lever arm 20. A pair of 3/32" diameter locking pins 25 that extend through both the second lever arm 20 and the second end 28 of the compression column 24.

The compression column 24 comprises an elongated bar preferably made of stainless steel and having a generally square or rectangular cross-sectional shape. Located adjacent each opposite end 26, 28 of the compression column 24 are connecting points. At each connecting point, two parallel flat rectangular prongs 30 extend longitudinally outward from each end 26, 28 of the compression column 24. Each prong 30 includes at least one circular through-bore for receiving a connecting pivot pin 32. The first lever arm 18 is pivotable about its pivot pin 32, but the locking pins 25 restrain the second lever arm 20 against pivoting motion.

The lever arms 18, 20 are shaped such that the distance between the arms 18, 20 is greater where the spring 15 extends between the arms 18, 20 than where the compression column 24 extends between the arms 18, 20. The lever arms 18, 20 are shaped this way so that they can support a spring that is longer and therefore able to exert a correspondingly more constant load for a given amount of specimen creep.

The lever arms 18, 20 are stainless steel bars with square or rectangular cross-sections. Preferably, each lever arm 18, 20 has a first linear section 34, 35 extending upwardly from the compression column 24. Each lever arm 18, 20 has a second linear section 36, 37 extending diagonally outward and upward from the first linear section 34. Finally, each lever arm 18, 20 has a third linear section 38, 39 extending vertically upward from the second linear section 36.

The third linear sections 38, 39 of the respective lever arms 18, 20 are generally parallel to one another when the test fixture 10 is in an unloaded state. Thus, the first 34 and third 38 linear sections of the first lever arm 18 extend in the same general direction but are axially offset from one another. Likewise, the first 35 and third 39 linear sections of the second lever arm 20 extend in the same general direction but are axially offset from one another.

The lever arms 18, 20 and, more specifically, the first segments 34, 35 of the respective lever aims 18, 20 are pivotally secured to the respective first and second mounting grips 12, 14 about respective pivot pins 40, 41. The mounting grips 12, 14 are secured to respective lower ends of the first linear sections 34, 35 of the lever arms 18, 20 outward of or below the compression column 24.

The force-applying assembly 22 is supported between the third, or upper linear sections 38, 39 of the lever arms 18, 20. As stated above, the lever arms 18, 20 extend upwardly from the grips 12, 14 and compression column 24 to distal third ends 38. Therefore, the compression column 24 is disposed between the grips 12, 14 and the force-applying assembly 22.

The force-applying assembly 22 includes the spring 15, which is a coil or helical spring, and a spring load adjuster 43. The spring load adjuster 43 includes a load bolt, which is a threaded eyebolt 44, and an eyebolt nut 45. The spring 15 is a tensile spring in that it is a relatively long spring designed and constructed to apply axially inward contracting force in response to axial outward extension. The tensile spring 15 is preferably designed so that an initially applied spring load will not decrease at a rate exceeding 3% of the initially applied spring load over 3000 hours. A first hooked end portion 47 of the spring 15 is detachably connected to the third end 38 of the first lever arm 18 by passing the hooked first end portion 47 of the spring 15 through an aperture 49 in the third end 38 of the first lever arm 18. A second hooked end portion 51 of the spring 15 is detachably connected to an eye portion 55 of the threaded eyebolt 44 by passing the second hooked end portion 51 through the eye portion 55 of the eyebolt 44. The spring 15 is detachably connected at each end to allow the spring 15 to be easily interchanged or replaced with springs having different spring rates.

A threaded shaft portion 57 of the eyebolt 44 extends laterally through an aperture 59 in the third linear section 39 of the second arm 20. The eyebolt nut 45 is threadedly engaged on the threaded shaft portion 57 of the threaded eyebolt 44 on an outer side of the second lever arm 20 opposite the spring 15. The eyebolt nut 45 is used to adjust the spring load and therefore the amount of resultant axial inward force the spring 15 applies to the lever arms 18, 20. More specifically, when the eyebolt nut 45 is tightened it causes the spring 15 to extend. In resisting that extension, the spring 15 applies inwardly directed axial force to the lever arms 18, 20, pulling them towards each other. The configuration of the arms 18, 20 and the position of the compression column 24 convert this inwardly-directed axial force to an axial outwardly-directed or tensile "stretching" force applied to a creep test specimen 16 connected between the grips 12, 14. In addition to re-directing the spring force, the shapes of the lever arms 18, 20 and the position of the compression column 24 also serve to multiply the force that the spring 15 applies to the specimen 16. In the preferred embodiment, the test fixture 10 is configured to apply a tensile force to a specimen 16 that is four times the force applied by the spring 15 to the third linear sections 38, 39 of the lever arms 18, 20.

The amount that the eyebolt nut 45 is turned precisely controls how much the eyebolt or loading bolt 44 extends the spring 15 and thus can be used to precisely control the amount of loading that the test fixture 10 imparts to a test specimen 16. To achieve a controlled loading rate, a variable-speed electrical motor can be used to turn the eyebolt nut 45. In addition, springs 15 with lower or higher loading spring constants can be interchanged as required to test materials of lower or higher stiffness.

Preferably, springs 15 used in the test fixture 10 are selected to have low spring constants (or extension rates). A spring having a lower spring constant will limit the decrease in spring force that results from test specimen creep. In other words, springs used in the test fixture 10 are preferably sized to maintain a nearly constant spring force even when a specimen 16 stretches. Springs 15 selected for use in the fixture will preferably have low spring constants that allow for no more than a three percent loading reduction over 3000 hours in response to specimen distention. It has been found, by using a test fixture 10 constructed according to the design disclosed herein, that the loading the fixture 10 applies to a test specimen 16 only decreases by approximately two percent as the test specimen 16 stretches. Thus, the fixture 10 does not unload to any significant degree as the test specimen 16 stretches.

Figure 2:
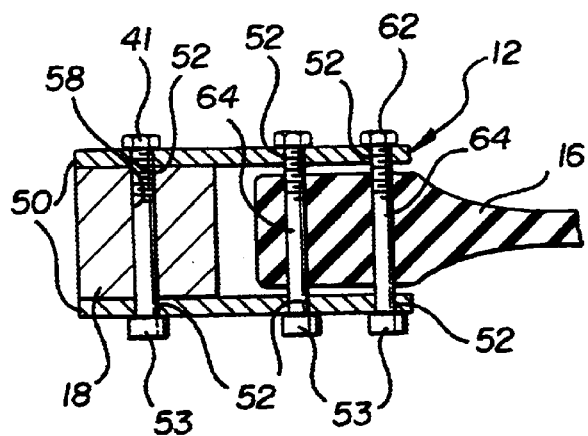
FIG. 2 is a cross-sectional view of the test fixture of FIG. 1 taken along lines 2—2 of FIG. 1.
Figure 3:
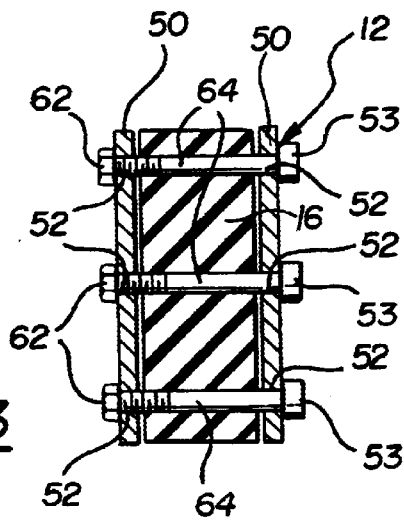
FIG. 3 is a cross-sectional view of the test fixture of FIG. 1 taken along lines 3—3 of FIG. 1.

Each mounting grip 12, 14 comprises a pair of parallel spaced-apart rectangular steel plates 50. As shown in FIGS. 2 and 3, each mounting grip plate 50 includes an identical pattern of seven holes 52 for receiving mounting pins 53 and pivot pins 40, 41. Six of the holes 52 are arranged on the inner half 54 of each plate 50 in two transversely oriented parallel rows of three, as best seen in FIG. 1. The remaining hole is disposed through an outer half 56 of each plate.

The outer halves 56 of each plate 50 of the first mounting grip 12 are disposed flush against opposite surfaces of the first lever arm 18. Likewise, the outer halves 56 of the plates 50 of the second mounting grip 14 are disposed flush against opposite surfaces of the second lever arm 20. A through hole shown at 58 in FIG. 2 passes through each lever arm 18, 20 and is co-axially aligned with the holes 52 disposed in the outer halves 56 of the plate 50. A threaded connecting pivot pin 53 passes through each of the co-axially aligned holes 52, 58 to pivotally fasten each set of plates 50 to their respective lever arms 18, 20.

For each mounting grip 12, 14, the center two of the holes 52 in the inner end 54 of each plate 50 are axially aligned with each other. Threaded pins 53 extend through each of these sets of co-axially-aligned holes and through holes 58 in the test specimen 16 to hold the test specimen 16 in place. Nuts 62 threadingly engage threaded ends of each pin 53 to hold the pins 53 in place. As shown in FIG. 3, threaded pins 53 also extend through the remaining four sets of holes 52 in each pair of mounting grip plates 50 and are fastened in place by nuts 62 at their threaded ends.

In practice, a precise amount of constant tensile stress can be applied to one or more creep test specimens 16 by selectively installing one of the test specimens 16 at a time in the fixture 10. Specifically, a test specimen 16 is secured to the mounting grips 12, 14 by first drilling six holes 64 in each end of the test specimen 16 as best shown in FIG. 3. The ends of the specimen 16 are then inserted between the spaced apart rectangular steel plates 50 of each mounting grip 12, 14. The six drilled holes 64 in each end of the specimen 16 are aligned with the holes 52 on the inner end 54 of each plate. Threaded mounting pins 53 are then inserted through each of these sets of co-axially-aligned holes to hold the test specimen 16 in place. Nuts 62 are then screwed on to the threaded ends of the pins 53 to hold the pins in place.

A tensile spring 15 for the fixture 10 is selected to have a spring rate that is less than or equal to an ultimate strength or "break strength" value of the test specimen 16. Generally, the ultimate strength of the test specimen 16 is given to a spring manufacturer who then designs a spring to compensate for the material in the specimen 16.

Opposite ends of the selected spring 15 are connected to respective spring attachment points on the lever arms 18, 20 such that the spring 15 applies a generally constant axial inward load to the lever arms 18, 20 and the lever arms apply a generally constant tensile load to the test specimen 16. A first end of the selected spring 15 is connected to the first lever arm and a second end of the spring 15 is connected to the eye portion of the eyebolt of the spring load adjuster 43.

Next, the spring load adjuster 43 is actuate to set a predetermined desired spring load by adjusting the loading bolt. The loading bolt is adjusted by turning the eyebolt nut 45 to extend the spring 15 until the spring 15 applies sufficient force to the third linear sections 28, 29 of the lever arms 18, 20 such that, when transmitted and multiplied through the lever arms 18, 20, a desired amount of force is applied to the test specimen 16. The eyebolt nut 45 may be turned by engaging the eyebolt nut 45 with a powered nut driver and actuating the nut driver. Once the force applying assembly 22 is adjusted, the specimen 16 and test fixture 10 are placed in a desirable test environment, such as under a ground vehicle for road testing.

The creep recovery characteristic of a test specimen 16 can be measured by, in addition to the above, measuring the resulting strain exhibited in the test specimen 16, returning the spring 15 to a relaxed condition, i.e. to the spring's "initial zero point", by backing out the eyebolt nut 45 of the spring load adjuster 43. Any resulting decrease in strain exhibited in the test specimen 16 is then measured. The difference between max strain and permanent strain is the creep recovery characteristic of the test specimen 16.

A test fixture 10 constructed according to the present invention saves substantial costs over stationary dead-weight creep testers. The device is compact and portable and relatively inexpensive. Further, it has been found that a device constructed in accordance with the present invention provides results comparable to stationary dead-weight creep testers. A graph comparing creep strain versus time results for the subject invention to those of a stationary dead-weight creep tester are shown in FIG. 4.

Figure 4:
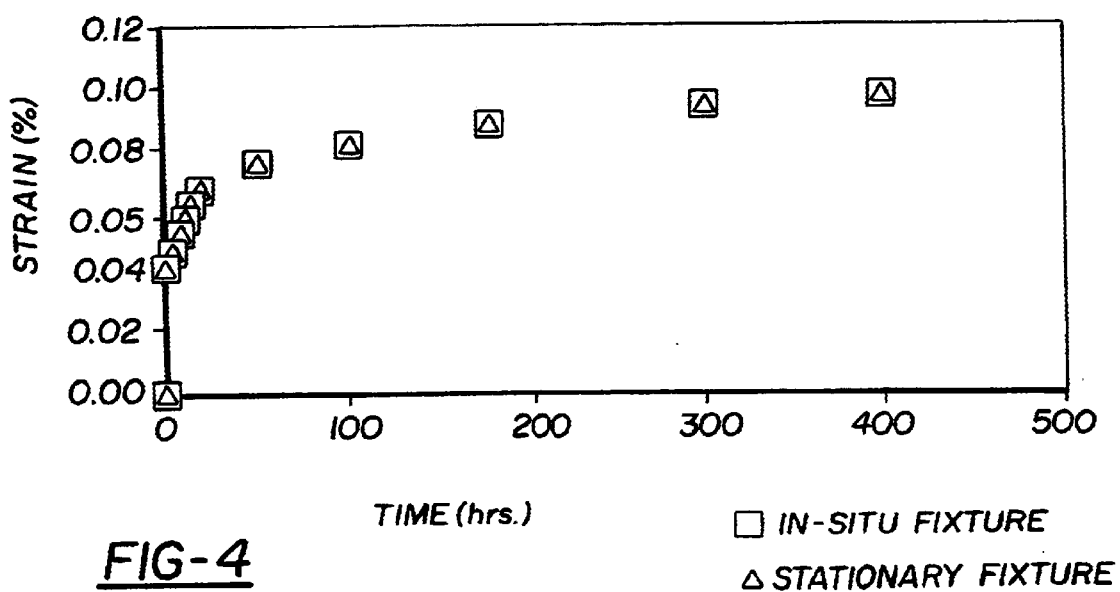
FIG. 4 is a graph comparing creep test results of deadweight creep machines and a fixture constructed according to the present invention.
Figure 5:
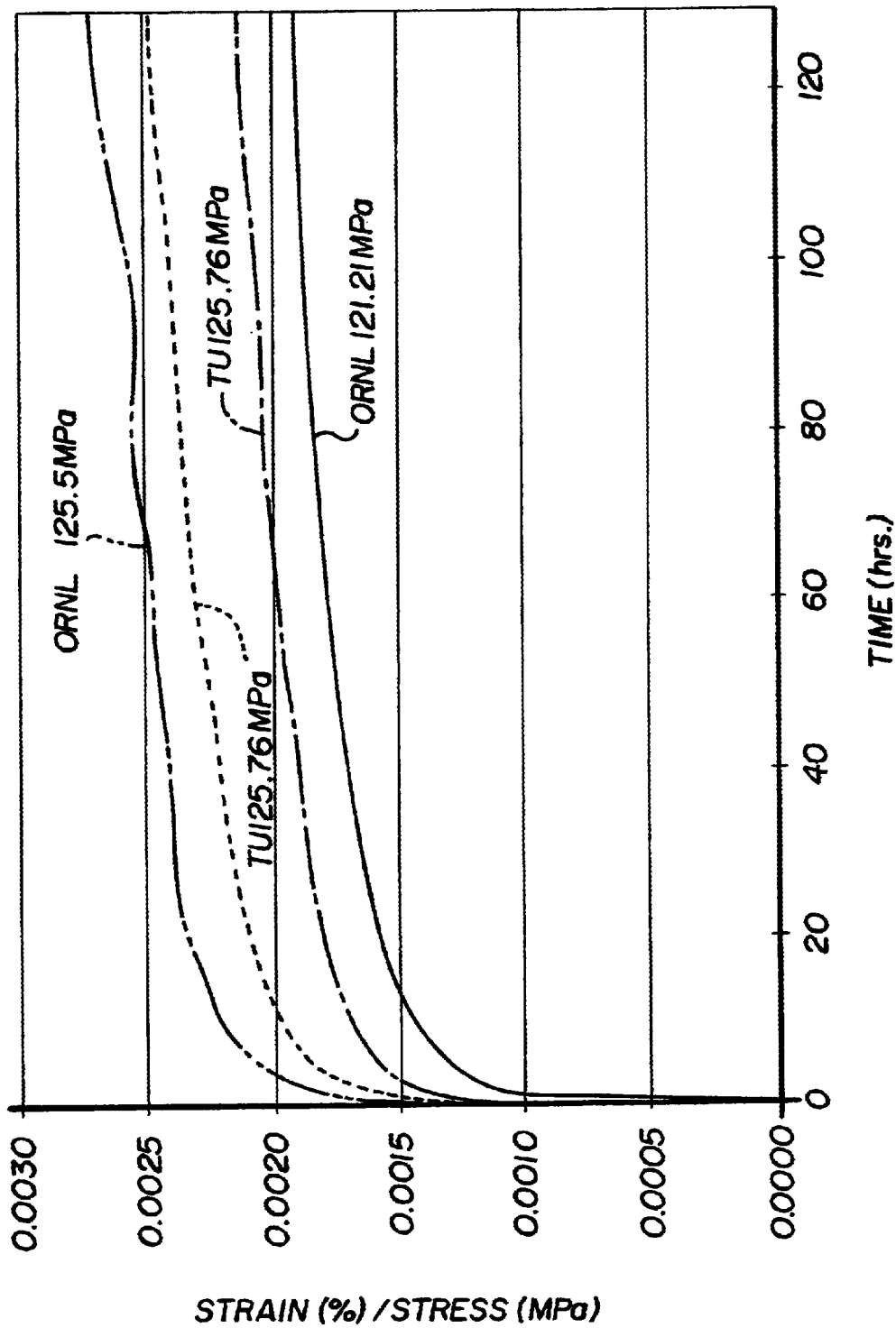
FIG. 5 is a graph comparing the creep compliance (strain/stress) of deadweight creep machines and a fixture constructed according to the present invention.

As shown in FIG. 4, the two sets of data are virtually indistinguishable. Further, FIG 5 shows a graph that compares creep compliance (strain divided by stress) produced over time by a test fixture 10 constructed according to the invention, to the amount of creep compliance produced over an equivalent time period by known stationary dead-weight creep testers. The lines in FIG. 5 that represent the creep compliance of the stationary dead-weight creep testers are the upper and lower lines designed "ORNL". The lines representing the creep compliance of the test fixture 10 made in accordance with the present invention are the middle two lines designated "TU". In other words, both lines representing the creep compliance of the test fixture 10 made in accordance with the present invention appear intermediate to the lines representing the creep compliance of the stationary dead-weight creep testers. This illustrates, as stated above, that data produced by the device made in accordance with the present invention is comparable to data produced by dead-weight creep testers.

This description is intended to illustrate certain embodiments of the invention rather than to limit the invention. Therefore, it uses descriptive rather than limiting words. Obviously, it's possible to modify this invention from what the description teaches. Within the scope of the claims, one may practice the invention other than as described.

What is claimed is:

1. A creep testing fixture for applying a precise amount of constant tensile stress to a creep test specimen to allow for precise measurement of creep in the test specimen, the fixture comprising:
    first and second mounting grips for holding opposite ends of a test specimen;
    a frame supporting the first and second mounting grips for relative reciprocal movement toward and away from each other;
    a spring connected between the first and second mounting grips, the frame being configured to subject a test specimen held between the mounting grips to tensile stress in response to force that the spring applies to the frame; and
    the spring is a tensile spring and the frame and spring are configured to subject a test specimen to tensile stress in response to axially inward force that the tensile spring applies to the frame such that spring load loss over time is limited by an amount sufficient to allow for accurate tensile creep testing of the test specimen.

2. A creep testing fixture as defined in claim 1 in which the tensile spring is designed so that spring load will not decrease more than 5% from an initially applied spring load over 3000 hours.

3. A creep testing fixture as defined in claim 2 in which the tensile spring is designed so that spring load will not decrease more than 3% from the initially applied spring load over 3000 hours.

4. A creep testing fixture as defined in claim 1 in which:
    the frame comprises a pivoted lever arm frame structure that includes a compression column connected between first and second lever arms;
    the spring is connected between the first and second lever arms; and
    the first and second mounting grips are supported on the first and second lever arms at respective points along the lever arms so that the compression column is positioned between and generally parallel to the spring and a test specimen held between the grips.

5. A creep testing fixture as defined in claim 4 in which the lever arms are shaped such that the distance between the arms is greater where the spring extends between the arms than where the compression column extends between the arms.

6. A creep testing fixture as defined in claim 4 in which the compression column:
    is pivotally connected to the first lever arm; and
    is fixed against pivotal motion to the second lever arm.

7. A creep testing fixture as defined in claim 1 in which: the fixture includes a spring load adjuster connected to the second lever arm; and the spring is connected at a first end to the first lever arm and at a second end to the spring load adjuster.

8. A creep testing fixture as defined in claim 7 in which the spring load adjuster includes:
    an eyebolt having a shaft portion that extends through an aperture in the second lever arm; and
    a nut threadedly supported on the shaft portion on a side of the second lever arm opposite an eye portion of the eyebolt.

9. A creep-testing fixture as defined in claim 1 in which the fixture is configured to allow springs to be removably connected between the lever arms.

10. A method for applying a precise amount of constant tensile stress to a creep test specimen to allow for precise measurement of creep in the test specimen, the method including the steps of:
    providing a test fixture having first and second mounting grips, a frame supporting the first and second mounting grips for relative reciprocal movement toward and away from each other, a spring connected between the first and second mounting grips, the frame being configured to subject a test specimen held between the mounting grips to tensile stress in response to axially inward force that the tensile spring applies to the mounting grips;
    providing a tensile test specimen having an ultimate strength value;
    providing a tensile spring having a spring rate equal to or less than the ultimate strength of the test specimen;
    connecting opposite ends of the tensile test specimen to the respective first and second mounting grips; and connecting opposite ends of the spring to respective spring attachment points on the lever arms such that the spring applies a generally constant axial inward load to the lever arms and the lever arms apply a generally constant tensile load to the test specimen.

11. The method of claim 10 in which:

the step of providing a test fixture includes providing a test fixture including a spring load adjuster connected to the second lever am, and the step of connecting opposite ends of the spring includes:

connecting a first end of the spring to the first lever arm; and connecting the second end of the spring to the spring load adjuster.

12. The method of claim 11 including the additional step of actuating the spring load adjuster to set a predetermined desired spring load.

13. The method of claim 12 including the additional step of actuating the spring load adjuster by turning the nut on the shaft portion of the eyebolt of the spring load adjuster.

14. The method of claim 13 including the additional step of turning the nut by engaging the nut with a powered nut driver and actuating the nut driver.

15. A method of measuring creep recovery, the method including the steps of:

providing a test fixture having first and second mounting grips, a frame supporting the first and second mounting grips for relative reciprocal movement toward and away from each other, a spring connected between the first and second mounting grips, the frame being configured to subject a test specimen held between the mounting grips to tensile stress in response to axially inward force that the tensile spring applies to the mounting grips;

providing a tensile test specimen having an ultimate strength value;

providing a tensile spring having a spring rate equal to or less than the ultimate strength of the test specimen;

connecting opposite ends of the tensile test specimen to the respective first and second mounting grips;

connecting opposite ends of the spring to respective spring attachments points on the lever arms such that the spring applies a generally constant axial inward load to the lever arms and the lever arms apply a generally constant tensile load to the test specimen;

measuring the resulting strain exhibited in the test specimen; returning the spring to a relaxed condition; and measuring any resulting decrease in strain exhibited in the test specimen.

16. The method of claim 15 in which:

the step of providing a test fixture includes providing a test fixture including a spring load adjuster connected to the second lever arm, the spring load adjuster including an eyebolt having a shaft portion that extends through an aperture in the second lever arm, and a nut threadedly supported on the shaft portion on a side of the second lever arm opposite an eye portion of the eyebolt; and the step of returning the spring to a relaxed condition includes backing out the nut on the spring load adjuster.

* * * * *

UNITED STATES PATENT AND TRADEMARK OFFICE
CERTIFICATE OF CORRECTION

PATENT NO. : 6,647,802 B2
DATED : November 18, 2003
INVENTOR(S) : Kelly Willson-Hackworth et al.

It is certified that error appears in the above-identified patent and that said Letters Patent is hereby corrected as shown below:

Column 2,
Line 65, after "one can" delete "applying" and insert -- apply --

Column 3,
Line 12, after "spring" delete "attachments" and insert -- attachment --

Column 4,
Line 6, after "spring" delete "L5" and insert -- 15 --
Line 52, after "lever" delete "aims" and insert -- arms --

Column 6,
Line 60, after "43 is" delete "actuate" and insert -- actuated --

Column 10,
Line 12, after "spring" delete "attachments" and insert -- attachment --

Signed and Sealed this

Twenty-second Day of June, 2004

JON W. DUDAS
*Acting Director of the United States Patent and Trademark Office*